(12) United States Patent
Cole

(10) Patent No.: US 8,091,439 B2
(45) Date of Patent: Jan. 10, 2012

(54) ANALYTE EXTRACTION PROBE ASSEMBLY

(75) Inventor: Alun Cole, Glyn Ogwn (GB)

(73) Assignee: Markes International Limited, Mid Glamorgan (GB)

( * ) Notice: Subject to any disclaimer, the term of this patent is extended or adjusted under 35 U.S.C. 154(b) by 597 days.

(21) Appl. No.: 10/577,501

(22) PCT Filed: Oct. 27, 2004

(86) PCT No.: PCT/GB2004/004532
§ 371 (c)(1),
(2), (4) Date: Dec. 27, 2006

(87) PCT Pub. No.: WO2005/043129
PCT Pub. Date: May 12, 2005

(65) Prior Publication Data
US 2007/0220996 A1 Sep. 27, 2007

(30) Foreign Application Priority Data
Oct. 27, 2003 (GB) .................................. 0325001.6

(51) Int. Cl.
*G01N 1/10* (2006.01)
(52) U.S. Cl. .......................... 73/864; 73/864.01; 422/69
(58) Field of Classification Search ............... 73/864.01, 73/864; 422/69
See application file for complete search history.

(56) References Cited

U.S. PATENT DOCUMENTS

| | | | | |
|---|---|---|---|---|
| 2,911,291 A | * | 11/1959 | Engel | 422/191 |
| 2,943,062 A | * | 6/1960 | Mader | 48/127.9 |
| 4,107,041 A | * | 8/1978 | Karlson | 210/198.2 |
| 4,225,575 A | * | 9/1980 | Piasio et al. | 436/518 |
| 4,911,026 A | | 3/1990 | Keives | |
| 5,496,741 A | | 3/1996 | Pawliszyn et al. | |
| 5,695,721 A | * | 12/1997 | Kitagawa et al. | 422/99 |
| 6,042,787 A | * | 3/2000 | Pawliszyn | 73/864.81 |
| 6,114,172 A | | 9/2000 | Siepmann et al. | |
| 6,420,187 B1 | | 7/2002 | Gilmore et al. | |
| 2002/0098594 A1 | | 7/2002 | Sandra et al. | |
| 2005/0137500 A1 | * | 6/2005 | Wingler | 600/562 |
| 2007/0209453 A1 | * | 9/2007 | Akinbo et al. | 73/864.71 |

FOREIGN PATENT DOCUMENTS

| | | |
|---|---|---|
| DE | 3803352 | 8/1989 |
| DE | 196 19 790 | 12/1996 |
| DE | 29917794 | 3/2000 |
| EP | 0548765 | 6/1993 |
| JP | 09101243 A * | 4/1997 |
| SU | 675340 | 7/1979 |
| WO | WO 01/57515 | 8/2001 |

* cited by examiner

*Primary Examiner* — Hezron E Williams
*Assistant Examiner* — Nishmiya Fayyaz
(74) *Attorney, Agent, or Firm* — Tumey L.L.P.

(57) ABSTRACT

A probe assembly for use in the extraction of analytes from a sample, which probe includes an elongate cylinder portion which is arranged to rotate about its longitudinal axis, and having thereon one or more vanes extending away from the cylinder portion.

17 Claims, 6 Drawing Sheets

ANALYTE EXTRACTION PROBE ASSEMBLY

BACKGROUND OF THE INVENTION

The present invention is concerned with a probe for use in the extraction of analytes from a sample.

There are many instances where it is necessary to analyse for components within a liquid, for example in the measurement of water and food quality. The method widely used in these applications include the use of gas chromatography or gas chromatography interfaced with mass spectrometry. However, before these components can be analysed by gas chromatography, they must be present in the gas phase.

A number of techniques are available to extract organic material from the liquid phase into the gas phase.

These include equilibrium headspace, purge and trap and solid phase extraction (SPE)

Equilibrium headspace is a technique where the components in the liquid phase are allowed to partition into the gas phase above the surface of the sample. After a period during which the partition into the gas phase may be enhanced by heating and agitation of the liquid, an equilibrium is established between the components in the liquid and the gas phase. The gas phase is then transferred to the analyser for analysis.

Unlike Equilibrium Headspace, in purge and trap, the gas above the liquid is continuously replaced with new gas. As a result, no equilibrium is formed and eventually virtually all the components are extracted from the liquid. As large volumes of purge gas may be required to extract all the components from the liquid, an adsorbent trap is typically used to reduce the sample volume before GC.

While Headspace and purge and trap are suited for components with a high solubility in the gas they are less efficient for components with low vapour pressure or of high soluability in the liquid. In these cases SPE may be more appropriate. In this case the components are extracted from the liquid using a solid (phase) absorbent and subsequently recovered into the gas phase using thermal desorption.

However it has been difficult to combine automation with the most efficient extraction.

One attempt to automate the process is termed Solid Phase Micro Extraction (SPME). In this approach the absorbent used to extract the component from the liquid, is coated on a fibre as a thin layer. The fibre is immersed in the sample for a time and then passed directly to the GC where it is thermally desorbed. As the fibres replace the conventional needles, the process is compatible with normal liquid autosampler that are widely available for GC. In this way there may be some degree of automation The disadvantage with SPME is that only a limited amount of adsorbent can be loaded onto a fibre. Since the process requires equilibrium between the two phases, the extraction efficiency depends on the mass of solid phase. As a result the SPME suffers from a low capacity for the components.

In an attempt to address this, the solid phase has been coated onto rods placed in the sample. The increased size of the rod permits a higher degree of coating and with it improved extraction efficiency. To increase the efficiency further such solid phase may be coated onto a magnetic stirring element. These are made to rotate with a magnetic stirrer. Further extraction efficiency may be achieved through sonic agitation. Alternatively the solid phase may be coated onto a non-magnetic stirring element with the liquid stirred using some other means. As with fibres, the rods are then thermally desorbed to release the components to the GC.

However such rods are not readily compatible with conventional autosampler. The current practice is to manually, in turn, remove the rod, wash with suitable wash solution (usually water) and dry using paper. The rods are then manually loaded into a desorption tube It is therefore an aim of the present invention to alleviate at least some of the disadvantages identified above.

It is a further aim of the present invention to provide a probe for use in extracting analytes from a sample.

It is a further aim to provide a probe which is suitable for use with an automated process.

BRIEF SUMMARY OF SOME OF THE PREFERRED EMBODIMENTS

Therefore, according to a first aspect of the present invention, there is provided a probe assembly for use in the extraction of analytes from a sample, which probe includes an elongate cylinder portion which is arranged to rotate about its longitudinal axis, and having thereon one or more vanes extending away from the cylinder portion.

The probe of the present invention may be coated with solid phase as a means for extracting materials; it does not depend upon the solid phase being coated on a magnetic stirring element, or upon there being a separate means of stirring the liquid. Furthermore, the probe may be used in an arrangement whereby the device can be processed from extraction through to thermal desorption substantially without any manual contact with the device and thereby offer the possibility of substantially full automation.

To ensure optimum extraction efficiency, the probe is shaped to maximise the area of the solid phase on the probe that is in contact with the liquid phase. It is also preferable that the shape causes movement within the liquid such that there is a continuous exchange of liquid in contact with the solid phase. This improves the extraction efficiency.

In contrast to other forms of rotating the element, such as magnetic stirring, the extracting element is connected directly to the means of rotation. As a result, the element may be easily moved into and out of the sample. This enables the device to be mechanically transferred to a solution to wash the solid phase, if necessary, assisted by further rotating of the device and then to be transferred to a desorption oven where the material can be released by heating It is particularly preferred that the probe is arranged to be an impeller in the sample.

The probe is typically arranged to be rotated in the sample. It is therefore envisaged that the probe further includes a rotating device. Alternatively, if the probe does not include a rotating device, it is envisaged a sample receptacle which contains the sample may be rotated.

The sample may be a fluid, powder, gel, foam, or the like. However, the probe is particularly suitable for use in extraction of analytes from a liquid phase.

The vane may be in the form of paddles, shoulders, blades or the like, extending from the cylinder portion. However, in a particularly preferred embodiment, the vane is arranged to extend substantially around the cylinder portion so as to form a spiral thread (typically extending along the length of the cylinder portion).

It is envisaged that the elongate cylinder and/or the vanes may be coated with a sorbent coating such as a polymethylsiloxane, polyethylene glycol, silicone, polyimide, octadecylchlorosilane, polymethylvinyl chlorosilane, liquid crystal polyacrylates, grafted self organised monomolecular layers and inorganic coating materials. However, it should be noted that the choice of coating may be specific to the analyte being analysed.

Accordingly, there is provided a probe assembly for use in the extraction of analytes from a sample, which probe includes an elongate cylinder portion which is arranged to rotate about its longitudinal axis, and having thereon one or more vanes extending away from the cylinder portion, the elongate cylinder and/or the vanes are coated with a sorbent material.

The probe assembly is substantially as described hereinbefore.

It is envisaged that the elongate cylinder is substantially hollow along its length. Such an arrangement is particularly suitable for purge and trap type extraction.

In this embodiment, it is envisaged that the hollow cylinder includes one or more apertures or perforations. The apertures being arranged to permit gas to flow through the walls of the cylinder. Alternatively, the probe may include a sparger, such as a sintered glass frit to provide a diffuse stream of gas bubbles. It is, of course, envisaged that the hollow cylinder apertures or perforations, may also have a sorbent coating.

Accordingly, there is further provided a probe assembly for use in the extraction of analytes from a sample, which probe includes an elongate cylinder portion which is arranged to rotate about its longitudinal axis, and having thereon one or more vanes extending away from the cylinder portion, the elongate cylinder portion is substantially hollow along its length and includes one or more apertures or perforations.

The probe assembly is substantially as described hereinbefore.

According to a further embodiment of the present invention, the probe further includes a sheath. The sheath is typically manufactured from an inert material such as glass or stainless steel. The sheath advantageously protects the surface of the elongate cylinder. The sheath may be arranged to pierce or penetrate a septum or the like when the probe is in use.

It is particularly preferred that the sheath and the elongate cylinder are movable relative to each other along the longitudinal axis of the elongate cylinder.

The present invention therefore further extends to a probe assembly for use in the extraction of analytes from a sample, which probe includes an elongate cylinder portion which is arranged to rotate about its longitudinal axis, and having thereon one or more vanes extending away from the cylinder portion, wherein the elongate cylinder portion is sheathed by a sheath member.

The probe assembly is substantially as described hereinbefore.

Therefore, it is preferred that the probe assembly further includes an elevation device. The elevation device is arranged to move the elongate cylinder relative to the sheath.

In this embodiment, it is envisaged that an internal surface of the sheath and/or the elongate cylinder may be coated. The coating is substantially as described hereinbefore with reference to the coating on the elongate cylinder. It is further envisaged that the coating on the elongate cylinder may be a different coating to that on the sheath (for example, a polar coating on the cylinder and non-polar coating on the sheath). This is particularly advantageous when differing analytes are being extracted from the sample.

According to yet a further embodiment of the present invention, it is envisaged that the probe further includes a heating device. The heating device may be a heater cartridge, element or the like. This is particularly advantageous during analysis of the extracted analyte, or during a desorption stage.

Accordingly, there is further provided a probe assembly for use in the extraction of analytes from a sample, which probe includes an elongate cylinder portion which is arranged to rotate about its longitudinal axis and having thereon one or more vanes extending away from the cylinder portion, and a heating device.

The probe is substantially as described hereinbefore.

The probe assembly may further include a housing. The housing typically includes at least one inlet and at least one outlet arranged to permit entry and exit of gas to the probe assembly.

BRIEF DESCRIPTION OF THE DRAWINGS

The present invention will now be described by way of example only, with reference to the "accompanying drawings, wherein.

DETAILED DESCRIPTION OF THE PREFERRED EMBODIMENTS

Figure 1:
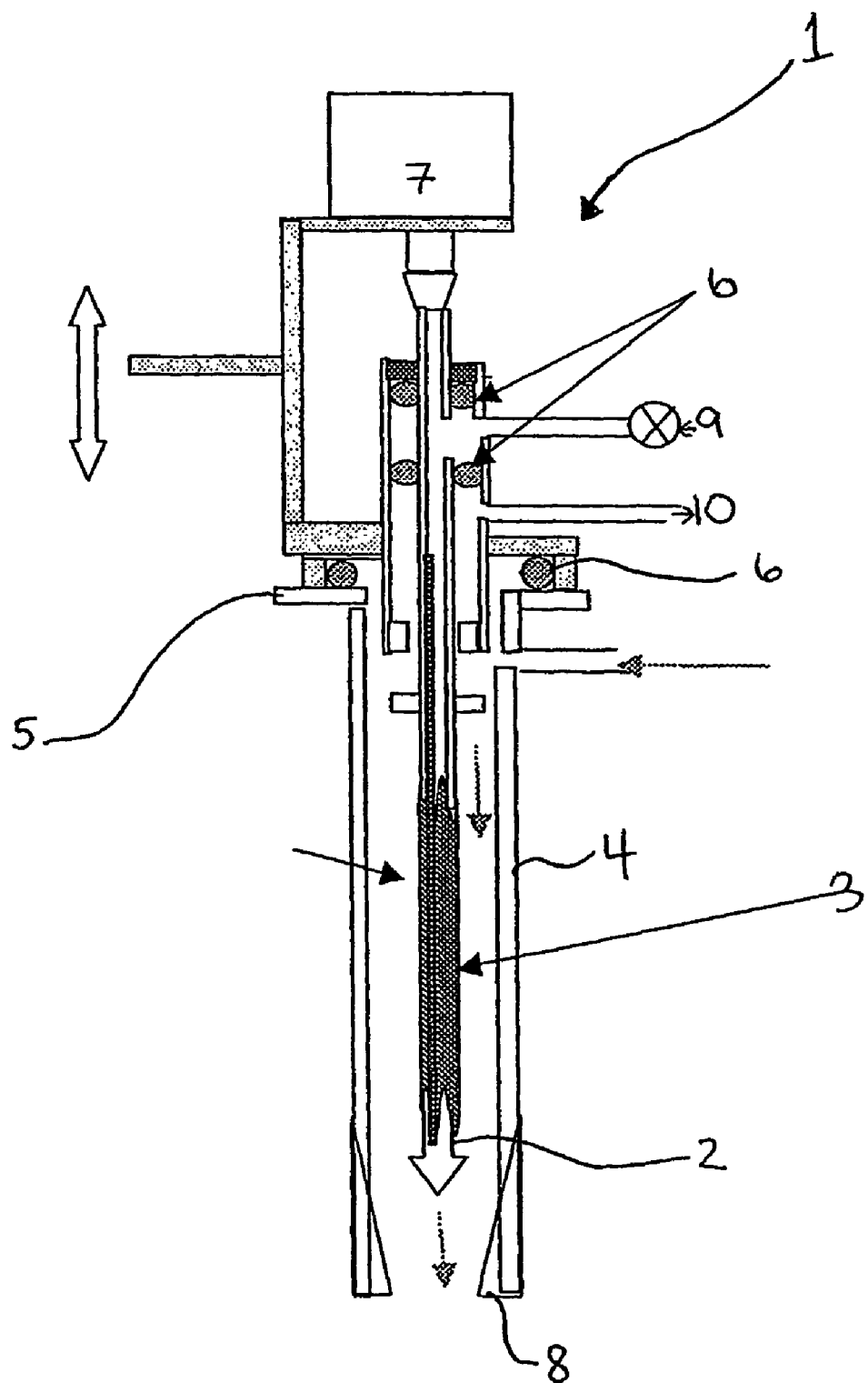
FIG. 1 represents a probe assembly according to the present invention.
Figure 2:
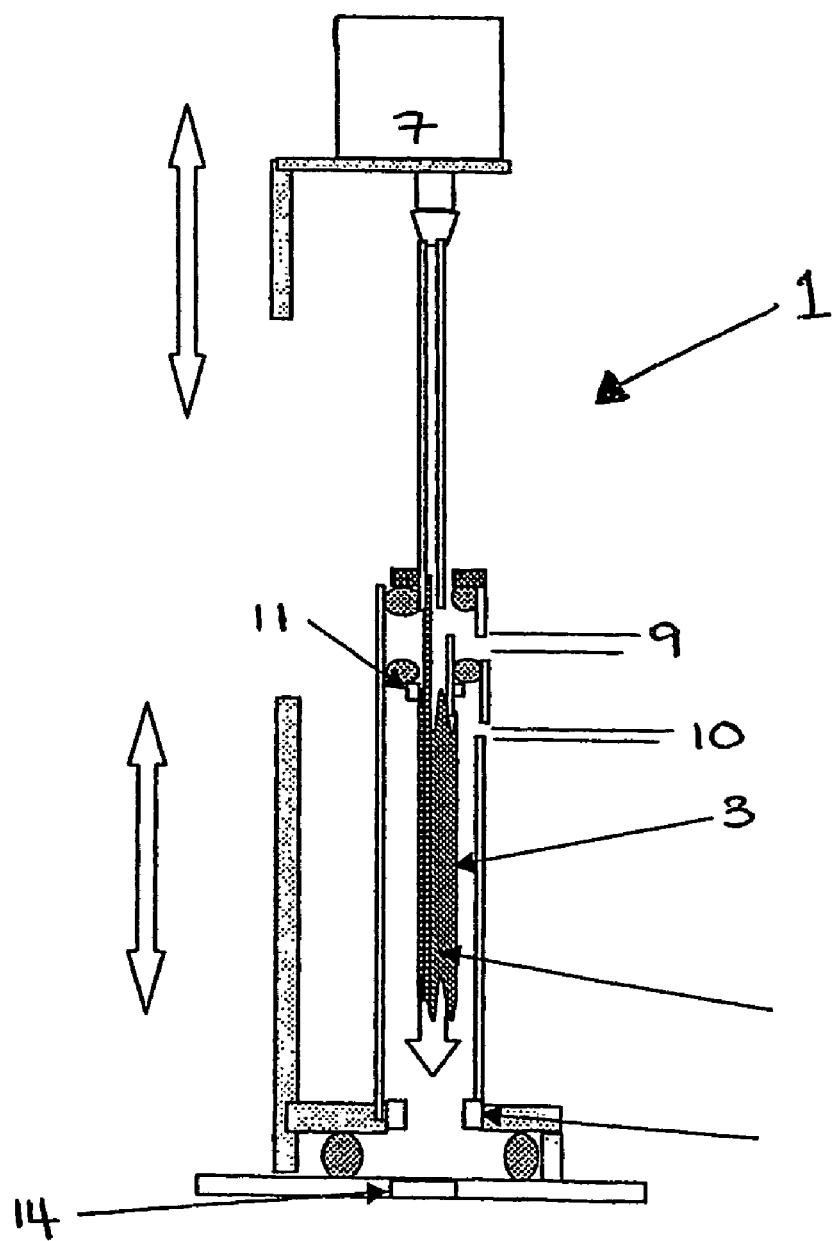
FIG. 2 represents a purge and trap/solid phase adsorption phase probe assembly before use.
Figure 3:
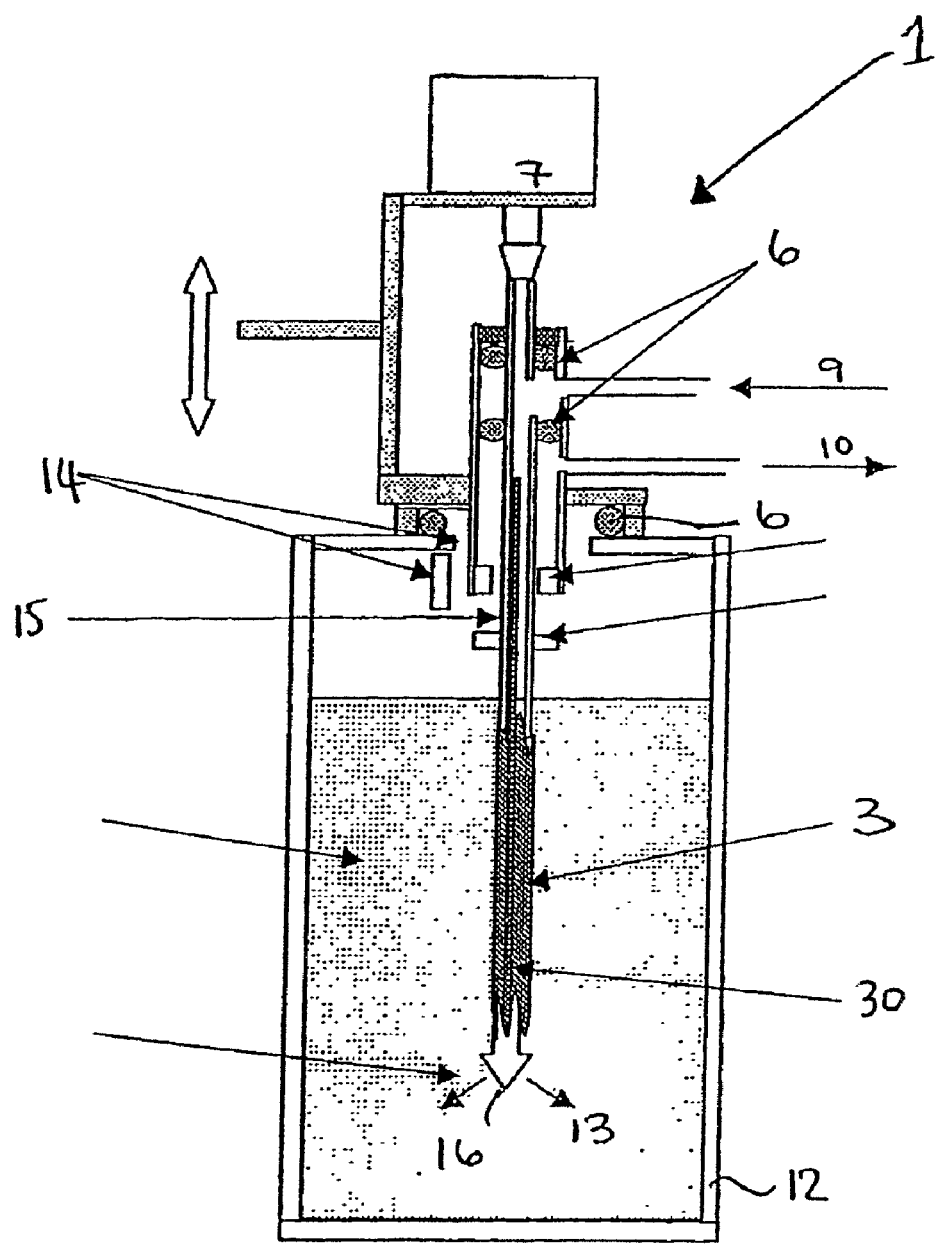
FIG. 3 represents a purge and trap/solid phase adsorption phase probe assembly during extraction.
Figure 4:
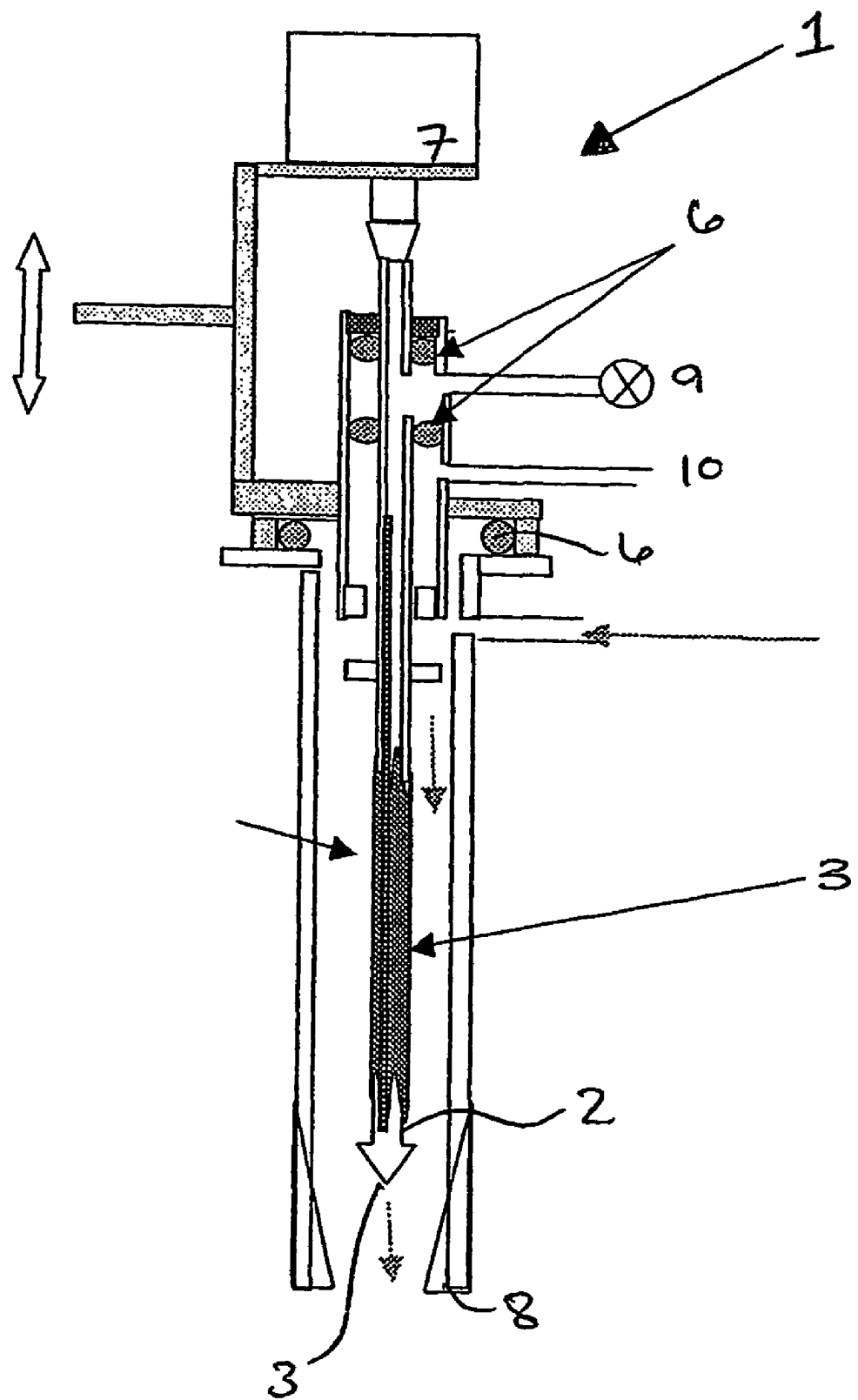
FIG. 4 represents a purge and trap/solid phase adsorption phase probe assembly during wash cycle.
Figure 5:
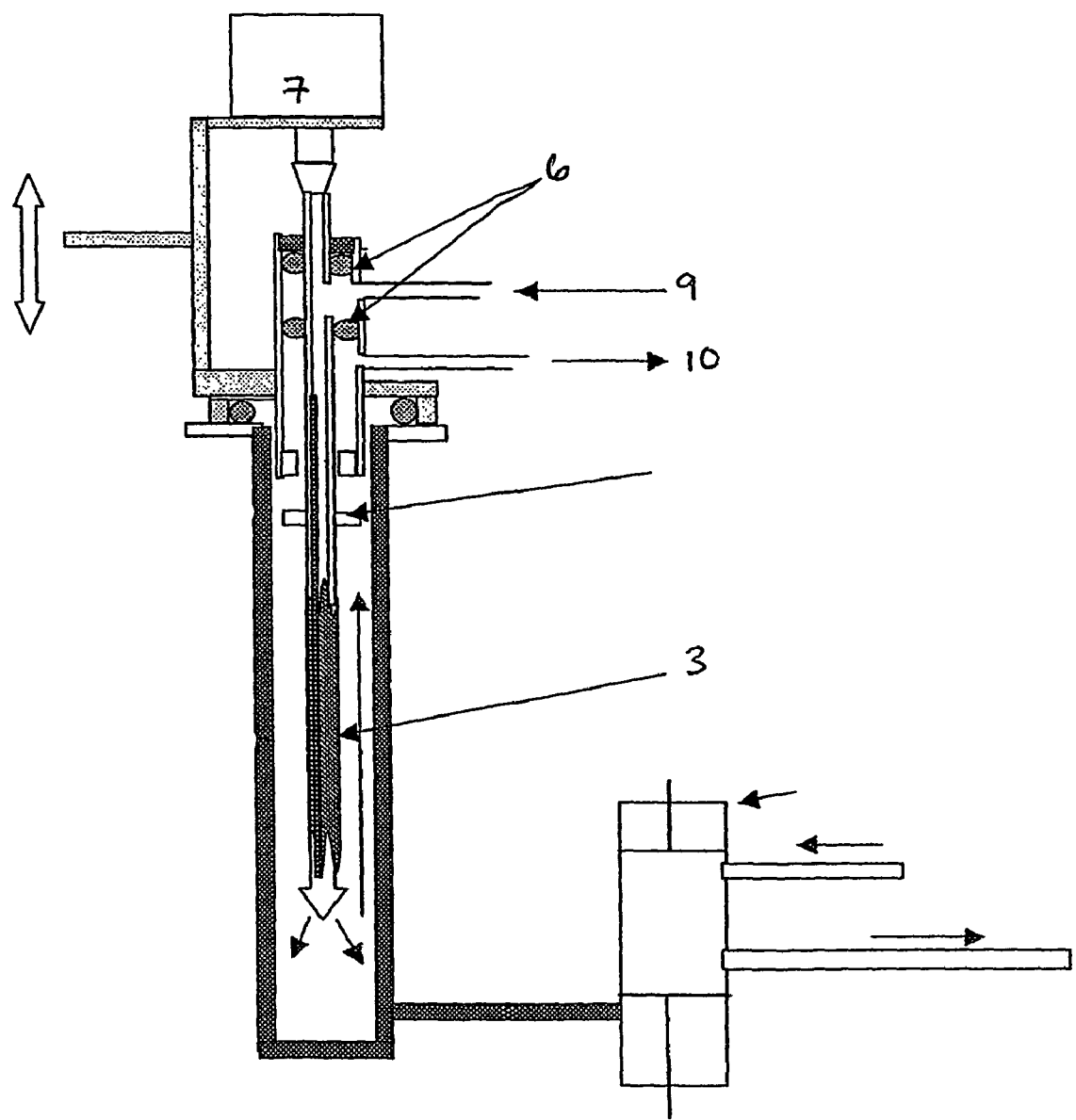
FIG. 5 represents a purge and trap/solid phase adsorption phase probe assembly during drying stage.
Figure 6:
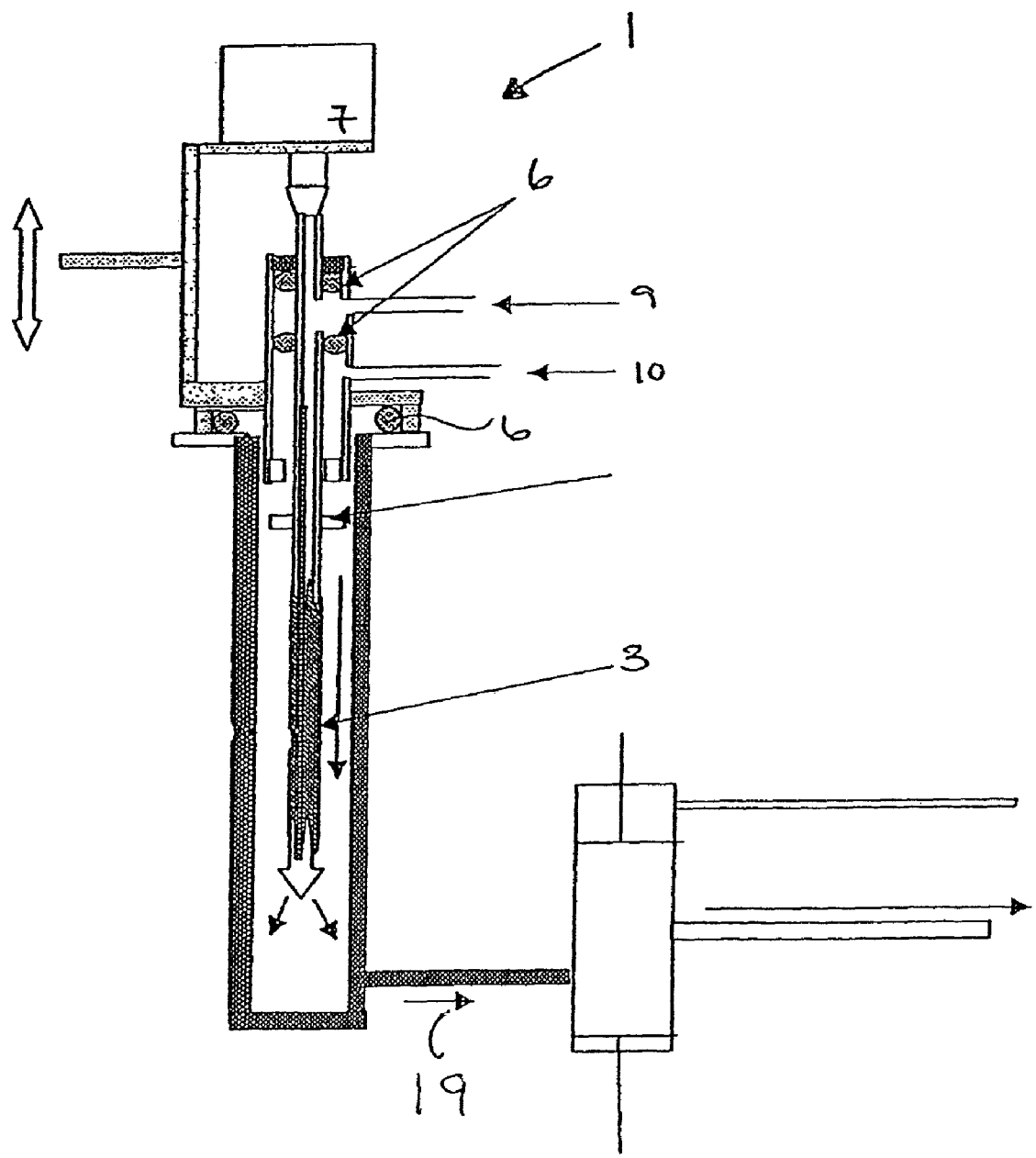
FIG. 6 represents a purge and trap/solid phase adsorption phase probe assembly during the desorption stage.

Referring to the Figures where like numerals have been used to represent like parts, there is provided a probe assembly generally indicated by the numeral 1. The probe assembly 1 comprises a stainless steel cylinder 2 having a spiral vane 3 about its outer surface. The spiral vane is coated with a sorbent coating.

A stainless steel sheath 4 is arranged to sheath (and therefore protect) the coating on cylinder 2. Housing 5 is maintained in a substantially airtight state using o-rings 6.

The probe assembly 1 is further provided with motor 7 which permits both longitudinal movement of cylinder 2 in sheath 4 and rotational movement of cylinder 2 about its longitudinal axis.

The housing 5 further includes an inlet port 9 for introducing gas into the probe assembly 1, and gas outlet 10 for exit of gas from the probe assembly Threaded connector 11 permits inter change of coated section on vane 3. This is particularly advantageous as it may be desirable to change the coating on the cylinder 2, thereby rendering the cylinder 2 substantially reusable and not disposable.

In use, probe 1 is positioned above sample vessel 12 containing sample 13; sample vessel 12 is sealed by 'crimp-on' septum 14 having a knock out plug 15.

Motor 7 is switched to an on position so that sheath 4 is driven through septum 14 and plug 15 is completely or partially knocked out. Cylinder 2 is moved in its longitudinal direction so that it is immersed in sample 13.

A flow of gas through inlet 9 is permitted so that purge gas exits sparger 16. Excess gas is then permitted to exit the probe assembly 1 via gas outlet 10 where it may be transferred via a trap to an analyser.

The cylinder 2 is rotated in sample receptacle 12 so as to ensure efficiency of adsorption of analyte onto the coated surface of vane 3.

After a predetermined period of time, cylinder 2 is removed from sample receptacle 12 and introduced to cleaning station 8. Cleaning fluid enters probe assembly via fluid inlet 17 so as to wash debris or foreign material from coated surface of vane 3 through drain 18 (whilst permitting adsorbed analyte to remain on the coated surface). During the wash phase, the cylinder 2 may be rotated to assist efficiency of washing.

Following the washing phase, the cylinder 2 is dried to remove excess moisture (which would have adverse affects during analysis by GC or GC/MS). The cylinder 2 is dried by forcing gas such as nitrogen through inlet 10, around coated surface 3 and out of outlet 18. At this time heating element 30 may also be turned on so as to assist in evaporation of water. Alternatively, the cylinder 2 may be rotated so as to obtain a 'spin-dry' effect.

Following the drying stage, the probe is transferred (by automated process) to a desorption chamber. The desorption chamber and/or the probe assembly is heated to assist in desorption. Desorption gas (which would be specific to the analyte being tested) is introduced via inlet 10.

During desorption, the desorption gas containing the analyte is transferred via transfer line 19 trap arrangement 20 to an analyser 21. It is preferable that this trap is the same as used for purge and trap.

The invention claimed is:

1. A probe assembly for use in the extraction of analytes from a liquid sample, which probe includes an elongate cylinder portion, a motor which is arranged to rotate the elongate cylinder portion about a longitudinal axis of the elongate cylinder portion and to move the elongate cylinder portion longitudinally to enable the cylinder to be immersed or removed from a sample vessel containing the liquid, and the elongate cylinder portion having thereon one or more vanes extending away from the cylinder portion, wherein the one or more vanes are coated with a solid phase as a means for extracting materials from the liquid sample in the sample vessel, and wherein the elongate cylinder portion is substantially hollow to allow gas to flow therethrough.

2. A probe assembly according to claim 1, wherein the probe is shaped to maximise the area of the solid phase on the probe that is in contact with a liquid phase.

3. A probe assembly according to claim 1, wherein the probe is arranged to be an impeller in the sample.

4. A probe assembly according to claim 1, wherein the one or more vanes are in the form of paddles, shoulders, or blades, extending from the cylinder portion.

5. A probe assembly according to claim 1, wherein the elongate cylinder and/or the vanes are coated with a sorbent coating.

6. A probe assembly according to claim 1, wherein the hollow elongate cylinder includes one or more apertures or perforations, the apertures or perforations being arranged to permit gas to flow through the walls of the cylinder, or wherein the probe includes a sparger, to provide a diffuse stream of gas bubbles.

7. A probe assembly according to claim 1, wherein the probe further includes a sheath.

8. A probe assembly according to claim 7, wherein an internal surface of the sheath and/or the elongate cylinder are coated.

9. A probe assembly according to claim 1, wherein the probe includes a heating device.

10. A probe assembly according to claim 1, which includes a housing having at least one inlet and at least one outlet arranged to permit entry and exit of gas to the probe assembly.

11. A probe assembly according to claim 4, wherein the one or more vanes are arranged to extend substantially around the cylinder portion so as to form a spiral thread.

12. A probe assembly according to claim 5, wherein the sorbent coating comprises polymethylsiloxane, polyethylene glycol, silicone, polyimide, octadecylchlorosilane, polymethylvinyl chlorosilane, liquid crystal polyacrylates, grafted self organised monomolecular layers or inorganic coating materials.

13. A probe assembly according to claim 6, wherein the sparger comprises a sintered glass frit.

14. A probe assembly according to claim 7, wherein the sheath is arranged to pierce or penetrate a septum.

15. A probe assembly according to claim 2, wherein the shape causes movement within the liquid such that there is a continuous exchange of liquid in contact with the solid phase.

16. A probe assembly for use in the extraction of analytes from a liquid sample, which probe includes a sheath and an elongate cylinder portion disposed within the sheath, wherein a motor is arranged to rotate the elongate cylinder portion about a longitudinal axis of the elongate cylinder portion and to move the elongate cylinder portion longitudinally within the sheath with a portion of the elongate cylinder portion moveable out of the sheath to enable the elongate cylinder portion to be immersed or removed from a sample vessel containing the liquid, and the elongate cylinder portion having thereon one or more vanes extending away from the elongate cylinder portion, wherein the one or more vanes are coated with a solid phase as a means for extracting materials from the liquid sample in the sample vessel, and wherein the elongate cylinder portion is substantially hollow to allow gas to flow therethrough.

17. A probe assembly for use in the extraction of analytes from a liquid sample, which probe includes an actuator and an elongate cylinder portion, wherein the elongate cylinder portion is arranged to rotate about a longitudinal axis of the elongate cylinder portion and to move longitudinally to enable the elongate cylinder portion to be immersed or removed from a sample vessel containing the liquid, and wherein the actuator actuates rotation of the elongate cylinder portion about the longitudinal axis and actuates longitudinal movement of the elongate cylinder portion, wherein the elongate cylinder portion has thereon one or more vanes extending away from the elongate cylinder portion, wherein the one or more vanes are coated with a solid phase as a means for extracting materials from the liquid sample in the sample vessel, and wherein the elongate cylinder portion is substantially hollow to allow gas to flow therethrough.

* * * * *